United States Patent [19]

Nguyen et al.

[11] Patent Number: 5,196,456

[45] Date of Patent: Mar. 23, 1993

[54] ACRYLATE SUPERABSORBENT POLYMERIZATION PROCESS

[75] Inventors: Hien V. Nguyen, East Windsor; Franklin Boardman, Englishtown, both of N.J.

[73] Assignee: Chicopee, New Brunswick, N.J.

[21] Appl. No.: 193,862

[22] Filed: May 13, 1988

Related U.S. Application Data

[63] Continuation of Ser. No. 94,200, Sep. 8, 1987, abandoned.

[51] Int. Cl.$^5$ .......................... C08F 2/46; C08F 20/06
[52] U.S. Cl. .......................... 522/81; 522/84; 522/182; 524/773; 524/785; 524/786; 524/832; 524/916; 526/93; 526/241
[58] Field of Search .................. 522/66, 81, 84, 182; 524/773, 785, 786, 832, 916; 526/93, 241

[56] References Cited

U.S. PATENT DOCUMENTS

| | | | |
|---|---|---|---|
| 4,024,040 | 5/1977 | Phalangas | 522/66 |
| 4,090,013 | 5/1978 | Ganslaw | 525/366 |
| 4,302,369 | 11/1981 | Elmquist | 524/734 |
| 4,354,487 | 10/1982 | Oczkowski | 522/72 |
| 4,443,492 | 4/1984 | Roller | 522/173 |
| 4,486,489 | 12/1984 | George | 522/84 |

*Primary Examiner*—David J. Buttner
*Attorney, Agent, or Firm*—Lawrence D. Schuler

[57] ABSTRACT

Superabsorbents made by the process of electron beam initiated polymerization of partially neutralized acrylic acid having improved absorbencies when a trivalent cationic salt, for example, Aluminum Acetate or a tetravalent cationic salt, for example, Platinum Tetrachloride, are added to the partially neutralized acrylic acid solution before polymerization is initiated.

3 Claims, No Drawings

ACRYLATE SUPERABSORBENT POLYMERIZATION PROCESS

This is a continuation of application Ser. No. 94,200, filed Sep. 8, 1987, now abandoned.

This invention relates to the process for polymerizing partially neutralized acrylic acid to prepare acrylate superabsorbents where the process involves the electron beam initiated polymerization of partially neutralized acrylic acid, and is more particularly concerned with obtaining improved superabsorbents by adding a multivalent cationic salt to the acrylic acid monomer before it is polymerized.

BACKGROUND OF THE INVENTION

It is known to produce superabsorbents commercially by polymerizing an acrylate salt with an electron beam. Such processes are described in the following patents:

Bashaw et al. U.S. Pat. No. 3,090,736 (assigned to Dow Chemical Company),

Ward, U.S. Pat. No. 4,192,727 (assigned to Union Carbide Corporation,) and

Oczkowski et al. U.S. Pat. No. 4,354,487 (assigned to Johnson & Johnson.

The final polymers thus produced, have an absorbent capacity and a swelling rate sufficient to be considered superabsorbents. However, industry is always seeking ways to improve the swelling capabilities of the polymer. It is especially desirable to find a process making use of currently available equipment and processing steps which involve merely the addition of various materials to the starting monomers and yet, result in the final product having improved swelling properties i.e. better absorbent capacity and faster swelling rate.

PRIOR ART

Multivalent cationic salts such as those which may be used in the present invention, are well known materials. They include such trivalent cationic salts as Aluminum salts and Lanthanium salts, and such tetravalent cationic salts as Platinum salts and Zirconium salts. In general they are salts of metals that are not transition metals and which do not undergo redox reactions. Some of them may have been used in connection with polymerization procedures, but not those procedures involved in the present invention.

The present invention involves the use of multivalent cationic salts to enhance absorbency in superabsorbents made by electron-beam initiated polymerizations. We do not say that the preparation of superabsorbents by electron-beam polymerization is novel or that electron-beam polymerization in general is novel. Monovalent or divalent cationic salts do not show this unexpected feature of absorbency enhancement, so their presence in the prior art of electron-beam polymerization is irrelevant to this invention. Such prior art includes:

U.S. Pat. No. 4,024,040: This describes a method of obtaining unusually high molecular weight water-soluble polymers, not superabsorbents, which must be water-insoluble. Aluminum salts are used at concentrations starting at 3%; in the instant invention the optimum concentration is between 1% and 2%.

In addition, aluminum salts are used only in conjunction with cationic or nonionic monomers. Since we use only an anionic monomers this patent makes our discovery that small concentrations of aluminum effect the polymerization of an anionic monomer even more surprising.

U.S. Pat. No. 4,090,013: The polymer described in this patent is cross-linked only by the trivalent aluminum cation. If the pH of the aqueous medium in which the polymer swells is adjusted to between 2.0 and 8.5 (see column 6, lines 24–36) the polymer dissolves. In our invention, the polymer is cross-linked covalently and the polymer in the presence or absence of aluminum cannot dissolve at any pH since it is not relying on ionic cross-linking to keep it insoluble. This inherent insolubility removes our polymer from the definition of claim 1 Sections a and c of this prior art patent.

U.S. Pat. No. 3,090,736: This patent does not address the effect of Al(III) and Pt(IV) in defined concentration on absorbency of the resultant polyacrylates. The patent mentions divalent, not tri- or tetravalent cations, but enhancement of absorbency due to their addition is not described.

U.S. Pat. No. 3,615,627: This patent describes a film material that is to be polymerized by light. Absorbency is not an issue in this patent, and therefore, the patent does not teach the enhancement of absorbency by multivalent cations in low concentration.

U.S. Pat. No. 3,764,502: This prior art patent describes a method of producing water soluble polymers of sodium acrylate via ionizing radiation. We are, however, in this patent interested only in water-insoluble polylmers. The polymer described may be used in conjunction with aluminum, but this metal is not part of the original formulation as true in our invention.

U.S. Pat. No. 3,839,076: In this patent acrylic acid is a minor component, water is not used as a solvent, and absorbency is not discussed. The patent, therefore, does not describe the effect of aluminum on enhancing absorbency in an aqueous polymerization.

U.S. Pat. No. 3,948,740: This patent teaches a process for making water soluble polymers and includes chemical initiation as well as radiation initiation. Metal salts of acrylates are used only when (and because) they are water soluble; the peculiar effect of aluminum is nowhere described in the patent.

SUMMARY OF THE INVENTION

This invention utilizes the process of producing an acrylate superabsorbent by the electron beam initiated polymerization of an aqueous monomer solution of partially neutralized acrylic acid, and adds to that known process the improvement resulting from the novel step of adding a multivalent cationic trivalent or tetravalent salt to the monomer solution before the polymerization begins, said salt being used in an amount sufficient to increase both the absorbent capacity and the swelling rate of the resultant acrylate superabsorbent. The most preferred multivalent cationic trivalent salt is Aluminum Acetate while the most preferred tetravalent salt is Platinum Tetrachloride. The aluminum salt is preferably added to the monomer solution either as a suspension or a solution, while the platinum salt will always wind up as a suspension due to its insolubility in aqueous systems.

DETAILED DESCRIPTION OF THE INVENTION

The present invention is based on the finding that multivalent cationic salts, such as Aluminum Acetate and Platinum Tetrachloride when added to acrylate monomer mix, affect in a positive manner the properties of the superabsorbents obtained by electron beam initiated polymerization, resulting in higher swelling capabilities for the final superabsorbent as contrasted to those conducted in an identical manner without the addition of the multivalent cationic salts.

The use of the process of the present invention offers a way to increase the absorbent capacity and swelling rate of the final superabsorbent, adds flexibility to the process, while still requiring only the extremely short reaction times customary for electron beam initiated polymerization of acrylate superabsorbents.

The starting material used in the present invention, is an aqueous monomer solution of partially neutralized acrylic acid. [It is the same monomer solution as previously used in the prior art process of making acrylate superabsorbents.] It is preferably 60% neutralized with potassium hydroxide and has a concentration by weight of total monomer of 65%. This starting monomer solution could vary as follows:

1. The acrylic acid can be neutralized with other bases such as Sodium hydroxide, ammonium hydroxide or even lithium hydroxide.
2. The degree of neutralization can be anywhere between 45% to 100%.
3. The monomer concentration is preferably as high as possible. The maximum solubility of the salt decreases as the degree of neutralization increases. In general we choose a concentration just below the solubility limit.

The multivalent cationic salts useful in the present invention include those of the following metals: Trivalent: Aluminum, Lanthanium; Tetravalent: Platinium, Zirconium. The cation should come from a non transition metal and one that do not undergo redox reactions.

The multivalent salts of the aforesaid metals can be either inorganic or organic salts. Examples of suitable inorganic salts include chlorides, nitrates, sulfates, borates, bromides, iodines, fluorides, mitrides, phosphates, and sulfides, such as aluminum chloride, aluminum sulfate, zirconium chloride, etc. Examples of suitable organic salts include salts of carboxylic acids such as carbonates, formates, acetates, butyrates, hexanoates, adipates, citrates, lactates, oxalates, oleates, propionates, salicylates, glycinates, glycollates and tartrates; for example, aluminum foroacetate, basic aluminum acetate, aluminum citrate, aluminum diformate, aluminum triformate, aluminum octate, zirconium lactate and zirconium acetate. Basic aluminum acetate is a preferred organic salt.

The ammonia and amine complexes (and especially those coordinated with ammonia) of these metals are particularly useful. Amines capable of so complexing include morpholine, monoethanol amine, diethylaminoethanol and ethylenediamine. Examples of these amine complexes include ammonium zirconyl carbonate, ammonium zirconyl glycinate, and ammonium zirconium chelate of nitrilotriacetic acid. Polyvalent metal complexes (salts) or organic acids that are capable of solubilization in the dispersing medium may also be employed. Such anions as acetate, glutamate, formate, carbonate, salicylate, glycollate, octoate, benzoate, gloconate, oxalate and lactate are satisfactory. Polyvalent metal chelates wherein the ligand is a bedentate amino acid, such as glycine or alanine are also useful.

The multivalent cationic salts for use in the process of the present invention may or may not be soluble in water. Where the salts are soluble they may be dissolved in water, and the resulting solution then added to the starting aqueous monomer solution of partially neutralized acrylic acid and dissolved into it.

Where the multivalent cationic salt is not soluble in water, it can be added to the starting aqueous monomer solution by being dispersed in powder form directly into the monomer solution to form a suspension. This method can be optionally used even where the salt is soluble in water. For example, one of the preferred multivalent salts, Platinum Tetrachloride, could only be added as a suspension, while another preferred multivalent salt, Aluminum Acetate, could be added either in the form of a suspension or a solution. Where it is added as a solution the typical preferred amount to use is on the order of a 10% solution, but this could be varied. The use of the multivalent salts in suspension form is more effective than in solution form in its effect on the demand absorbent capacity (grams of saline absorbed per gram of superabsorbent powder).

As will be evident from the examples shown in Table I, there is an optimum range of the amount of multivalent salt to be added and if too much salt is added the absorbent capacity may even be diminished. Another factor to be considered in determining the most desirable processing conditions here is the total radiation dose used. The enhancement of the swelling property of the final superabsorbent made by the process of electron beam initiated polymerization of partially neutralized acrylic acid, using the improvement of the present invention, is most evident in those cases where the total radiation dose is low.

In conducting the process of the present invention the monomer mass resulting from the addition of the multivalent cationic trivalent or tetravalent salt to the monomer solution was placed in plastic bags, which were then passed under an electron beam. Different samples were subjected to different doses i.e. megarads of electron beam radiation to initiate the polymerization. The resulting superabsorbent from each of the plastic bags was then dried, ground into sub 20-mesh powder and tested for its absorbent capacities. The test was conducted as follows:

The powder sample is weighed out in an amount close to 100 mg. It is then deposited uniformly on a pre-weighed glass filter paper, via a vacuum suction. The area deposited is about 20 cm$^2$. The filter paper with the powder sample on top and a weight corresponding to 0.02 psi pressure is then placed on a porous plate test cell of a Gravimetric Absorbency Tester (described in U.S. Pat. No.4,357,829); the test is thus started. The amount of saline absorbed as a function of time is plotted on a chart recorder. The amount of Saline absorbed after 30 minutes is recorded as Demand Absorbent Capacity.

The electron beam equipment used was an electro curtain machine made by Energy Science Inc., wherein the accelerating voltage is 300 KV. The results obtained are shown in Table I.

EXAMPLES

As shown in Table I, there is a control solution showing the effect of electron beam initiated polymerization at five (5) different radiation doses by the demand absorbent capacity at each dose. There is then shown the absorbent capacity for varying amounts of Aluminum Acetate in suspension, Aluminum Acetate in solution and Platinum Tetrachloride in suspension, each at various radiation doses.

In each case the starting solution (with or without the added multivalent cationic salt) was an aqueous monomer solution of partially neutralized acrylic acid, which was 60% neutralized with Potassium Hydroxide, at a concentration of 65%, by weight of total monomer. When the Aluminum Acetate was added in suspension, it was dispersed in the percentage by weight shown as a powder directly into the monomer solution to obtain a suspension. The same was true of the Platinum Tetrachloride which was used in suspension form only. When the Aluminum Acetate was added in solution the amount shown by weight was dissolved in water to make a 10% solution and that aqueous solution of Aluminum Acetate was dissolved into the monomer solution.

Table I summarizes the results. In the first row are control samples with no multivalent salt added. It appears that the samples polymerized with Aluminum Acetate (AlAc) added by either means clearly have higher absorbent capacities, especially at the low doses (0.27 MR and 0.67 MR). The same observations can be made with the Platinum Tetrachloride, but the effect of this salt is even stronger. The Aluminum Acetate suspension seems to have stronger and more consistent effect than the Aluminum Acetate salt in solution.

The suspension, which would not dissolve in the monomer solution even at the boiling point, disappears completely after polymerization to yield a clear gel.

The variation in the swelling of control samples (row 1) as function of dose where the increase is sharper at low doses and levels off at higher doses suggests that the extent of polymerization reaction, and the accompanying gel/sol ratio may be the principal factor. At low doses, addition of multivalent salts (cf. columns with doses 0.27 & 0.67 MR), especially in suspension, seems to cause sharp increase in the swelling. At higher doses the effect is not noticeable, i.e. it makes little difference at higher doses. Thus it would appear that the enhancement is via reaction kinetics. First the crosslinking effect of the multivalency helps to build up the apparent molecular weight early in the reaction and thus enhances the overall reaction rate. The Aluminum (and Platinum) atom is electron-dense and is a well known X-ray emitter when bombarded by electrons. This effect may have helped by increasing the effective radiation penetration to ensure more complete reaction in the whole volume of the sample.

The column for 1.33 MR seems to suggest that it is possible to add too much Aluminum Acetate, since somewhere between 2% and 3% Aluminum Acetate the effect seems to begin to lessen. The optimum amount of Aluminum Acetate suspension added may be somewhere between 1% and 2%.

In the case of Platinum Tetrachloride, the enhancement effect decreases somewhere between 0.6% and 1.5% levels which indicates that there seems to exist an optimum range of Platinum Tetrachloride as well.

TABLE I

| Formulation | Demand Absorbent Capacities (g saline/g powder) | | | | | |
|---|---|---|---|---|---|---|
| | | 0.27 | 0.67 | 1.33 | 2.67 | 5.2 |
| Monomer Solution Alone (control) | | 13 | 11.8 | 18.5 | 24.9 | 27.9 |
| Same wt. AlAc in Suspension | 1.0% | 18.7 | | 19.6 | | 30.1 |
| | 1.2% | 19.3 | 22.0 | 22.6 | 28.9 | |
| | 1.5% | | | 19.6 | | |
| | 2.0% | | | 20.0 | | |
| | 3.0% | | | 15.8 | | 29.4 |
| Same wt. AlAc in Solution | .33% | 16.9 | 17.5 | 20.5 | 26.4 | |
| | 1.0% | | | 17.8 | | |
| | 2.0 | | | 17.7 | | |
| Same wt. PtCl4 in Suspension | .6% | | 20.5 | 27.6 | 30.6 | |
| | 1.5% | | 16.7 | 20.4 | 23.7 | |

In terms of swelling rate, the samples with Aluminum or Platinum salt added also show considerable enhancement. The effect on rate is probably even more pronounced. Swelling rate is characterized by the initial absorbency rate, i.e. the initial slope of the absorbency-time curve. The initial rate for control samples with e-beam dose of 0.67 and 1.33 Megarads is in the range of 0.06–0.08 grams saline/second. For samples with 2% aluminum Acetate suspension the rate is around 0.3 grams/second. For samples with Pt Cl4 suspension the rates are even higher.

We claim:

1. In the process of producing a water-insoluble acrylate superabsorbent polymer by the electron beam initiated polymerization of an aqueous monomer solution of partially neutralized acrylic acid, the improvement comprising adding a tetravalent platinum salt to the monomer solution before polymerization, said salt being present in an amount ranging from about 0.3% to about 2% based on the weight of said solution, whereby both the absorbent capacity and the swelling rate of the resultant acrylate superabsorbent polymer are increased.

2. The process of claim 1 wherein the tetravalent platinum salt is Platinum Tetrachloride.

3. The process of claim 2 wherein the Platinum Tetrachloride is added to the monomer solution by being dispersed in powder form directly into the monomer solution to form a suspension.

* * * * *